(12) United States Patent
Brown

(10) Patent No.: US 11,058,857 B2
(45) Date of Patent: Jul. 13, 2021

(54) METHOD OF IMPRINTING TATTOO DESIGNS

(71) Applicant: Set Point Solutions, LLC, Tampa, FL (US)

(72) Inventor: Joseph Harrington Matanane Brown, Stafford, VA (US)

(73) Assignee: Set Point Solutions, LLC, Tampa, FL (US)

( * ) Notice: Subject to any disclaimer, the term of this patent is extended or adjusted under 35 U.S.C. 154(b) by 421 days.

(21) Appl. No.: 15/818,666

(22) Filed: Nov. 20, 2017

(65) Prior Publication Data
US 2018/0147400 A1    May 31, 2018

Related U.S. Application Data

(60) Provisional application No. 62/497,634, filed on Nov. 28, 2016.

(51) Int. Cl.
*A61M 37/00* (2006.01)
*G06T 1/00* (2006.01)
*H04N 9/31* (2006.01)

(52) U.S. Cl.
CPC .... *A61M 37/0084* (2013.01); *A61M 37/0076* (2013.01); *G06T 1/00* (2013.01); *A61M 2205/3306* (2013.01); *A61M 2205/50* (2013.01); *H04N 9/3185* (2013.01); *H04N 9/3188* (2013.01)

(58) Field of Classification Search
CPC .......... A61M 37/0076; A61M 37/0084; A61B 2018/00452; A61B 2017/00769; G03B 21/00; G03B 21/001; A01K 11/005
See application file for complete search history.

(56) References Cited

U.S. PATENT DOCUMENTS

| 6,299,307 | B1 | 10/2001 | Oltean et al. | |
|---|---|---|---|---|
| 7,249,712 | B2 | 7/2007 | Ingalls | |
| 7,922,688 | B2 | 4/2011 | Bodduluri et al. | |
| 8,036,448 | B2 * | 10/2011 | Gildenberg | A61B 34/70 382/153 |
| 9,371,957 | B2 | 6/2016 | Dallarosa | |
| 2011/0272976 | A1 * | 11/2011 | Wei | A47C 1/022 297/195.11 |
| 2012/0040314 | A1 * | 2/2012 | Rubino, Jr. | G06Q 30/02 434/81 |

(Continued)

FOREIGN PATENT DOCUMENTS

WO    WO 2015/193513    12/2015

*Primary Examiner* — Majid Jamialahmadi
(74) *Attorney, Agent, or Firm* — Middleton Reutlinger

(57) ABSTRACT

The method for automatically producing precise tattoo markings on any anatomical body portion automatically by providing a controlled articulated arm carrying a tattoo machine implement. The method also provides a multi-axis positioning platform for supporting and positioning a person, receiving a tattoo, in a prime, optimal, and comfortable position. Also, the method provides choosing, with a selector, a tattoo of choice from any data source of images, as well as applying, rectifying, and mapping, with a physical or virtual design projection and visualization media, the chosen tattoo to the person. The method completes a tattoo using the articulated arm with the tattoo machine implement producing a precise, accurate, and aesthetically pleasing tattoo, automatically.

16 Claims, 1 Drawing Sheet

(56) References Cited

U.S. PATENT DOCUMENTS

2016/0252803 A1* 9/2016 Moran ................ G03B 21/145
                                                                353/28
2016/0307057 A1  10/2016 Li et al.

* cited by examiner

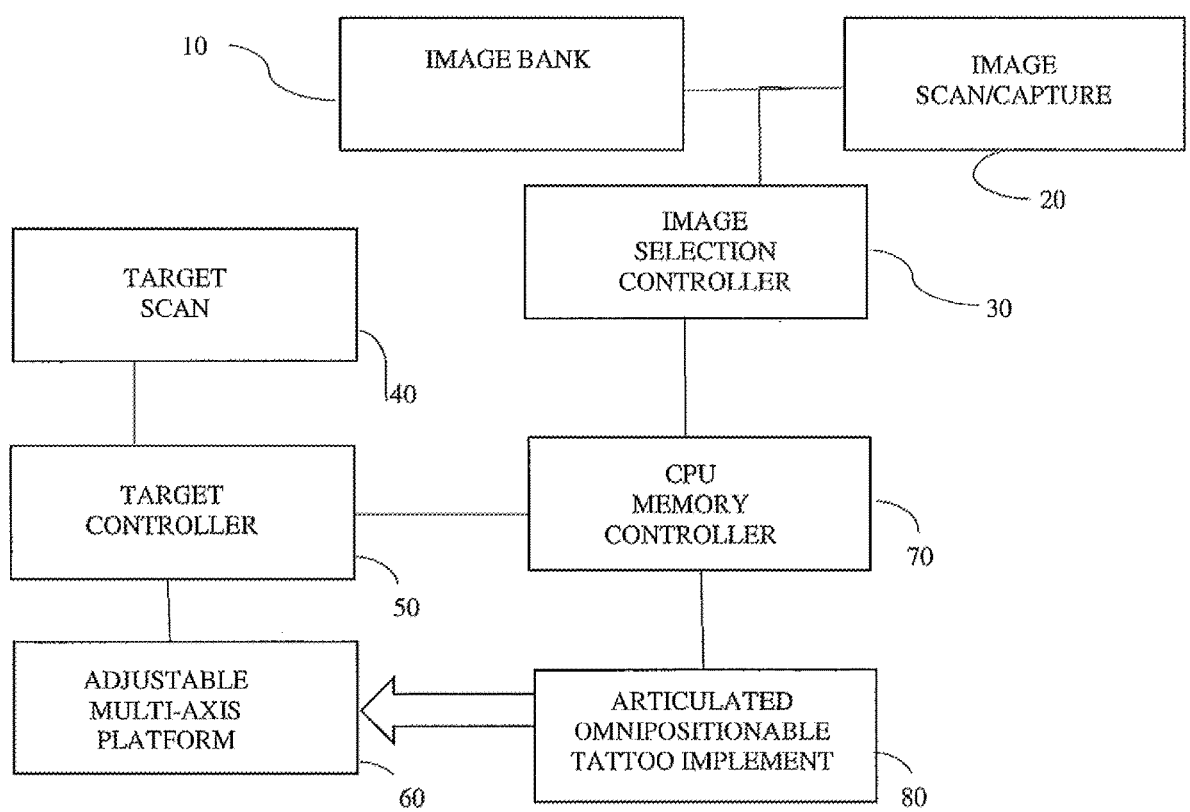

METHOD OF IMPRINTING TATTOO DESIGNS

RELATED APPLICATION DATA

The present application claims the benefit under 35 U.S.C. § 119 to U.S. provisional patent application Ser. No. 62/497,634, filed Nov. 28, 2016 and entitled "Precision Automated Tattoo," the disclosure of which are herein incorporated by reference.

BACKGROUND OF THE INVENTION

1. Field of the Invention

The present invention relates to a method of operating a tattoo system for generating and producing precise tattoo markings on any anatomical body portion automatically.

2. Description of the Related Art

The art of imprinting tattoos has been a part of human history, the existence of it dates as far as 12,000 years BCE. The purpose of tattooing has varied from culture to culture, and its place on the time line, but there are commonalties that prevail from the earliest known tattoos to those being done today. Tattoo art is more popular and accepted than it has ever been. All classes of people seek the best tattoo artists.

In some cultures, and in more primitive times, the pigment is placed on the skin and pushed in by needles or other relatively sharp objects held by hand, or pulled into the skin on thread that is passed into and out of the surface on a curved needle. Tattoo designs may be small and localized, or may be any size up to covering most or the entire skin surface.

The most common type of tattooing device is a reciprocating needle controlled by the operator as a hand-held tool that reciprocates rapidly, ordinarily between 50-3,000 times per minute, to inject non-water soluble pigment into skin in a desired pattern. If the injection is too deep, however, the pigment may not be easily visible through the surface or the features of the design may appear blurred. If the injection is too superficial, the pigment may not be held in proper position and may migrate to produce a similarly blurred image or the pigment may be gradually displaced as the dermis is recycled, resulting in a design that would appear muted and faded.

The application of permanent conventional tattoos generally involves the utilization of a needle that is controlled by the hand of the tattoo artist—this is inherently inexact, tedious, time consuming, laborious, and consequently expensive. Thus, a method for producing tattoos precisely, and solving the aforementioned problems of inexactness, extensive time, and extreme labor is desired.

SUMMARY OF THE INVENTION

In accordance with a general aspect of the invention disclosed herein, the method is provided for automatically imprinting precise tattoo designs. As described herein, the provided method could be used for all kinds of tattooing, including cosmetic, therapeutic, dermatological, as well as recreational or artistic tattooing.

An aspect of the inventive method includes automatically imprinting tattoo designs on any portion of an anatomical body, by selecting an image for tattooing, mapping the image on the portion of the anatomical body, positioning the body to optimize the mapping, controlling a tattoo implement to precisely trace the mapped image, and generating the tattoo image on the body through a fully automated system. Additionally, within the purview of the disclosure, the mapping would include physical and virtual. In that, the precise positioning of the tattoo (e.g., rotating, scaling, rectifying, etc.) would be tracked or view on a computer rendering (such as 3-dimensional imaging device). In such a manner, a consumer could see how the tattoo would appear on their selected body part (i.e., arm, chest, etc.), and have the ability to make modifications with a graphic artist.

These and other features of the present invention will become readily apparent upon further review of the following specification and drawing.

BRIEF DESCRIPTION OF THE DRAWINGS

FIG. 1 is a flow diagram illustrating the automated precision tattoo machine of the present invention.

Similar reference characters denote corresponding features consistently throughout the attached drawings.

DETAILED DESCRIPTION OF THE PREFERRED EMBODIMENTS

The method of automatically imprinting tattoo designs precisely on an anatomical body is disclosed herein with reference to the drawing FIGURE. In the drawing FIG. 1, the aspects are set forth in the present method for automatically imprinting tattoo designs on an anatomical body, a tattoo design is selected in the image selector 30 by the person receiving the tattoo. The image is chosen from a cache of images stored in a database image data bank 10, or user submitted by the image capture 20. The image capture 20 would include the ability for the design being created independently by a graphic/tattoo artist, or the design may also be scanned into the system from any other source of images, such as images found on the Internet, a media outlet, or a printing/painting supplied by the person receiving the tattoo. The image bank 10, the image capture 20, and the image selector 30 may operatively include an input/output unit, a memory unit, an image processing unit, an optical scanning unit, and any necessary power source, communication links, and controls.

A further aspect illustrated in FIG. 1, a tattoo recipient would identify an area or location on the body where the desired and chosen image, at image selector 30, would be applied. The method would place the recipient on a multi-axis platform 60. The multi-axis platform 60 would be any suitable multiple position chair or table that is capable of supporting the recipient. The multi-axis platform 60 would include straps, framework, or any suitable means for supporting the recipient in a comfortable yet stationary position, and provide optimal access to the location where the tattoo is to be applied. For example, if the tattoo is to be applied on the forearm of the recipient, the multi-axis platform 60 would be used to comfortably seat the recipient, and support and secure the forearm in a position to receive the tattoo without any unnecessary discomfort.

Once placed in position on the multi-axis platform 60, a target scan 40 communicates with a target controller 50 that analyzes the target location, determining size, contour, and anomalies. The target controller 50 also provides a mapping of the target location. The scan/map from the target controller 50 of the location and the selected image from the image selector 30 are combined in a CPU Memory Controller 70 so as to match the selected image to the target location so as to properly size and position the image to the target location. The color and amount of tattoo inks would be calculated also by the CPU Memory Controller 70.

The CPU Memory Controller 70 generates control signals based on the image map and ink calculations. The CPU Memory Controller 70 communicates with an articulated arm and tattoo implement 80 supported thereon. The communicated control signals are used by the articulated arm and tattoo implement 80 to maneuver about the target location on the recipient on the multi-axis platform 60.

The tattoo implement 80 moves meticulously about the target location, and generates and distributes the ink to the articulated arm and tattoo implement 80, producing the tattoo on the target location. The resultant image on the target location is a precisely sized and placed on the target location. The method utilizes computer aided design and computer aided manufacture programs in the CPU Memory Controller 70 for producing the tattoo image on the target location, and distributing the ink to the tattoo needle.

The method allows the person receiving the tattoo to present or identify the location on his body where the tattoo is to be applied. According to the method, the location is then scanned by an optical scanner that determines the contour of the location. The contour of the location is designated as target area. The method provides a mapping of the chosen image onto the chosen location. The method creates a mapped image on the chosen location, adjusting the image in accordance with the contour of the location. The amount of tattoo ink will be distributed in a manner to provide a precise inking based on mapped image onto the contour of the location.

Utilizing this method and process for tattooing gives the consumer greater peace of mind and confidence that the design that they want will be rendered into their skin exactly the way they envision it. The precision made possible by the utilization of robotic equipment, the integration of the three dimensional conformal printing, computer-aided graphic design software, and a gyroscopically stabilized device housing for tattoo implement 80 which is controlled by an operating system that incorporates micro-movement tracking technology, all enable the production of a tattooed design incorporating significant intricacies, exotic details, and maximum color palettes. In the current state of the art, the hand skill and strength of tattoo artisan, the size of the needle, and the implement used are limiting factors in the application of a tattoo design. The method set forth herein provides a systematic process that makes the imagination of the client the primary obstacle to a tattoo design.

It is to be understood that the present invention is not limited to the embodiments described above, but encompasses any and all embodiments within the scope of the following claims.

I claim:

1. A method for automatically imprinting tattoo designs on an anatomical body, comprising the steps of:
    selecting a tattoo image;
    identifying a skin target area on the anatomical body;
    scanning the skin target area;
    positioning the skin target area;
    mapping the tattoo image on the skin target area by sizing the tattoo image to fit the skin target area;
    positioning a tattoo machine implement in proximity to the skin target area;
    controlling the tattoo machine implement to trace the mapping of the tattoo image;
    operating the tattoo machine implement to apply tattoo ink automatically to the skin target area; and
    producing a precise tattoo image on the skin target area of the anatomical body.

2. The method according to claim 1, wherein the step of selecting the tattoo image includes retrieving a predetermined tattoo design from a database containing a plurality of tattoo designs.

3. The method according to claim 1, wherein the step of selecting the tattoo image includes producing an image design for a tattoo;
    whereby the produced image design is a computer aided design generation of direction vectors.

4. The method according to claim 1, wherein the step of scanning the skin target area includes identifying natural undulations of the skin target area.

5. The method according to claim 1, wherein the step of positioning the skin target area includes providing a multi-axis adjustable platform for presenting the skin target area of the anatomical body in a preferred optimal position for receiving the tattoo image.

6. The method according to claim 1, wherein the step of mapping the tattoo image on the skin target area further comprises the step of projecting the tattoo image onto the skin target area, sizing, and orienting elements of the projected image to optimally fit onto the skin target area.

7. The method according to claim 1, wherein the step of controlling the tattoo machine implement to trace the mapping of the image includes automatically operating the tattoo machine implement to pierce the skin target area to produce the precise tattoo image while following the trace of the tattoo image mapped on the skin target area.

8. The method according to claim 7, wherein the step of operating the tattoo machine implement includes applying the tattoo ink automatically to the skin target area during each pierce of the skin target area in response to the controlling of the tattoo machine implement.

9. A method for automatically identifying, mapping and imprinting an image design on an anatomical body, comprising the steps of:
    selecting the image design;
    identifying a target area on the anatomical body;
    scanning the target area on the anatomical body;
    pre-positioning the target area of the anatomical body for receiving the image design;
    mapping the image design on the target area of the anatomical body by sizing the image design to fit the target area;
    positioning a machine implement in proximity to the pre-positioned target area;
    controlling the machine implement to trace the mapped image design on the anatomical body;
    operating the machine implement to apply a printing media to the target area on the anatomical body; and
    producing a precise image design on the target area of the anatomical body with the printing media on the target area.

10. The method according to claim 9, wherein the step of selecting the image design includes retrieving a predetermined design from a database containing a plurality of image designs.

11. The method according to claim 9, wherein the step of selecting the image design includes producing the image design.

12. The method according to claim 9, wherein the step of scanning the target area includes identifying undulations in the target area.

13. The method according to claim 9, wherein the step of pre-positioning the target area includes providing a multi-axis adjustable platform for presenting the target area in a preferred optimal position for receiving the image design.

14. The method according to claim 9, wherein the step of mapping the image design on the target area includes the step of projecting the image design onto the target area, sizing, and orienting elements of the projected image design to optimally fit onto the target area.

15. The method according to claim 9, wherein the step of controlling the machine implement to trace the mapping of the image design includes automatically operating the machine implement to produce the precise image design while following the trace of the mapped image design on the target area.

16. The method according to claim 15, wherein the step of operating the machine implement includes automatically applying the printing media to the target area in response to the controlling of the machine implement.

* * * * *